(12) United States Patent
Takeuchi et al.

(10) Patent No.: US 8,017,329 B2
(45) Date of Patent: Sep. 13, 2011

(54) METHOD OF SCREENING BAFF SUPPRESSOR OR INHIBITOR

(75) Inventors: Tsutomu Takeuchi, Tokyo (JP); Kensei Tsuzaka, Tokyo (JP); Keiko Yoshimoto, Tokyo (JP)

(73) Assignees: Kowa Company, Ltd., Nagoya-shi (JP); Tsutomu Takeuchi, Tokyo (JP); Kensei Tsuzaka, Tokyo (JP); Keiko Yoshimoto, Tokyo (JP)

( * ) Notice: Subject to any disclaimer, the term of this patent is extended or adjusted under 35 U.S.C. 154(b) by 0 days.

(21) Appl. No.: 12/751,307

(22) Filed: Mar. 31, 2010

(65) Prior Publication Data

US 2010/0196948 A1 Aug. 5, 2010

Related U.S. Application Data

(62) Division of application No. 11/662,795, filed as application No. PCT/JP2005/016888 on Sep. 14, 2005, now Pat. No. 7,846,662.

(60) Provisional application No. 60/609,826, filed on Sep. 15, 2004.

(51) Int. Cl.
*C12Q 1/68* (2006.01)

(52) U.S. Cl. .......................... 435/6; 435/7.23

(58) Field of Classification Search ........................ None
See application file for complete search history.

(56) References Cited

FOREIGN PATENT DOCUMENTS

WO 98/18921 A1 5/1998

OTHER PUBLICATIONS

H. Ben-Bassat et al, "Establishment of a Human T-Acute Lymphoblastic Leukemia Cell Line with (16;20) Chromosome Translocation", Cancer Genet Cytogenet (1990) vol. 49, No. 2, pp. 241-248.
G. Cheema et al, "Elevated Serum B Lymphocyte Stimular Levels in Patients With Systemic Immue-Based Rheumatic Diseases", Arthritis & Rheumatism, vol. 44, pp. 1313-1319, 2001, American College of Rheumatology.
Supplementary European Search Report dated Apr. 23, 2008, issued in corresponding European Patent Application No. 05783483.0.
J. Groom et al, "Association of BAFF/BLyS Overexpression and Altered B Cell Differentiation with Sjoren's Syndrome", The Journal of Clinical Investigation, vol. 109, pp. 59-68, 2002.
B. Huard et al, "BAFF Production by Antigen-presenting Cells Provides T Cell Co-Stimulation", Int'l Immunology, Mar. 2004, vol. 16, No. 3, pp. 467-475.
Translation of International Preliminary Report on Patentability mailied Mar. 29, 2007 of international Application No. PCT/JP2005/016888.
S.D. Khare et al, "Severe B Cell Hyperplasia and Autoimmune Disease in TALL-1 Transgenic Mice", Proc. Nat'l Acad. Sci., USA, (2000), vol. 97, No. 7, pp. 3370-3375.
F. Lavie et al, "Expression of BAFF (BLys) in t Cells Infiltrating Labial Salivary Glands From Patients with Sjogren's Syndrome", Journal of Pathology, J Pothol 2004, 202, pp. 496.502, Hopital de Bicetre, Le Kremlin Bicetre, France.
F. Mackey et al, " Mice Transgenic for BAFF Develop Lymphocytic Disorders Along with Autoimmune Manifestations", The Journal of Experimental Medicine, vol. 190, pp. 1697-1710, 1999, The Rockefeller University Press.
R. Marienfeld et al, "Signal-Specific and Phosphorylation-Dependent ReIB Degradation: A Potential Mechanism of NF-kB Control", Oncogene (2001) 20m pp. 8142-8147, University of Wurzberg, germany.
P. Moore et al, "BLyS: Member of the Tumor Necrosis Factor Family and B Lymphocyte Stimulator", Science, vol. 285, No. 5425. pp. 260-263, 1999, human genome Sciences.
International Search Report of PCT/JP2005116888, mailing date of Dec. 20, 2005.
P. Schneider et al, "BAFF a novel Ligand of the Tumor Necrosis Factor Family, Stimulates B Cell Growth", The Rockefeller University Press, vol. 189, No. 11, Jun. 7, 1999, pp. 1747-1756.
H.B. Shu et al, "TALL-I is a novel Member of the TNF Family that is Down-Regulated by Mitogens", Journal of Leukocyte Biology, (1999), vol. 65, No. 5, pp. 680-683.
K. Yoshimoto et al, "Aberrant Expression of BAFF in T Cells of Systemic Lups Erythematosus, which is Recapitulated by a Human T cell Line, Loucy", International Immunology, vol. 18, No. 7, pp. 1189-1196, Japan.
J. Zhang et al, "Cutting Edge: A Role for B-Lymphocyte Stimular in Systemic Lupus Erythematosus", The Journal of Immunology, vol. 166, pp. 6-10, 2001, The American Association of Immunologyst.
D. Wu et al.; "Expression of THANK in human PBMC activated with different stimulator", Xibao Yu Fenzi Mianyixue Zazhi, (2002), vol. 17, No. 4, pp. 304-306, Cited in the int'l search report (w/English Abstract).
Zocchi, M. R. et al.; "Signal requirements for activation of leukaemic T cells from a chronic lymphocytic leukaemia ( T-CLL)"; Clin. Exp. Immunol., (1990), vol. 82, pp. 108-113.
Kawasaki, A. et al.; "Analysis on the association of Human BLYS ( BAFF, TNFSF13B) polymorphisms with systemic lupus erythematosus and rheumatoid arthritis"; Genes and Immunity, (2002), vol. 3, pp. 424-429.

*Primary Examiner* — Patricia A Duffy
(74) *Attorney, Agent, or Firm* — Westerman, Hattori, Daniels & Adrian, LLP

(57) ABSTRACT

A method of screening a novel BAFF suppressor or inhibitor. More specifically speaking, a method which comprises adding a combination of TPA with ionomycin and/or an anti-CD3 antibody to a cultured human cell to thereby induce the production of BAFF by the cell; a method of screening a substance capable of suppressing the expression or activity of BAFF which comprises adding a test substance to a BAFF-production system prepared by adding a combination of TPA with ionomycin and/or an anti-CD3 antibody to a cultured human cell and measuring the expression amount and/or the activity of BAFF in the BAFF-production system; and a BAFF production inducer for a BAFF-producing cell which contains a combination of TPA with ionomycin and/or an anti-CD3 antibody.

4 Claims, 5 Drawing Sheets

METHOD OF SCREENING BAFF SUPPRESSOR OR INHIBITOR

INCORPORATED-BY-REFERENCE TO RELATED APPLICATIONS

This application is a divisional application of U.S. Ser. No. 11/662,795, filed Mar. 14, 2007, which is a 371 National Stage of PCT/JP05/16888 and claims the benefit of priority of U.S. Provisional Application Ser. No. 60/609,826, filed on Sep. 15, 2004, the entire contents all of which are incorporated by reference.

TECHNICAL FIELD

The present invention relates to a method of screening a novel BAFF suppressor or inhibitor. The present invention relates particularly to a method of screening a substance suppressing or inhibiting the expression or production of BAFF by constructing a system wherein a detectable sufficient amount of BAFF is stably released extracellularly by subjecting a commercial cell strain to suitable stimulating conditions.

BACKGROUND ART

It is known that BAFF (B cell activating factor belonging to the TNF family) is produced and secreted from T cells, monocytes/macrophages, dendritic cells and the like and regulates such as B-cell differentiation, activation, survival rate via 3 types of receptors on B cells (Moore et al., Science, 285, 260-263 (1999)).

Human BAFF is a transmembrane form protein comprising 285 amino acids. There is a structural characteristic of trimer formation such as the presence of a cytoplasmic domain of 46 amino acids, an extracellular domain of 218 amino acids, and two N-glycosylation sites in its amino acid sequence. It is estimated that an extracellular domain of 152 amino acids from C-terminal is cleaved with a protease of Furin family and released in a soluble form. The amino acid sequence of human BAFF initially named neutrokine α was disclosed as SEQ ID NO: 1 or 2 in publication of International Patent Application WO98/18921. Other names of human BAFF such as Kay, TNFSF13B, Blys, TALL-1, THANK and zTNF4 are also known.

BAFF-R, TACI (transmembrane activator and calcium modulator and cyclophilin ligand interactor), and BCMA (B cell maturation antigen) are known as BAFF receptors. BAFF-R and BCMA are expressed mainly in B cells, and TACI is expressed in B cells and activated T cells.

The physiological action of BAFF lies in regulation of B-cell differentiation, activation, survival rate and the like as described above, and is increasingly revealed in recent years to participate in pathologic condition. That is, it is reported that a mouse expressing BAFF in excess shows SLE-like symptoms such as increase in peripheral blood B cells, enlargement of lymph nodes and spleen, increase in IgG level in serum, antinuclear antibody production, deposition of immune complex in the kidney, albuminuria and nephritis (Mackay et al., J. Exp. Med., 190, 1697-1710, (1999), and Khare et al., Proc. Natl. Acad. Sci. USA 97, 3370-3375, (2000)). It was further reveled that this mouse also shows SS-like symptoms such as inflammation of salivary gland and destruction of salivary gland with advancing age (Groom et al., J. Clin. Invest., 109, 59-68, (2002)). An increase of BAFF level in serum in patients suffering from SLE, RA and SS is also reported (Zhang et al., J. Immunol., 166, 6-10, (2001); Cheema et al., Arthritis Rheum., 44, 1313-1319, (2001); and Groom et al., J. Clin. Invest., 109, 59-68, (2002)), and there are also many reports such as higher BAFF level in synovial fluid than in serum in patients suffering from RA (Cheema et al., Arthritis Rheum., 44, 1313-1319, (2001)), expression of BAFF in salivary gland-infiltrating leukocytes in patients suffering from SS (Groom et al., J. Clin. Invest. 109, 59-68, (2002)), correlation between serum BAFF level in patients suffering from SLE and immunoglobulin or anti-ds DNA antibody (Zhang et al., J. Immunol. 166, 6-10, (2001)) and correlation between BAFF in patients suffering from RA and rheumatoid factor (Cheema et al., Arthritis Rheum., 44, 1313-1319, (2001)).

From these facts, it can be said that the suppression or inhibition of expression or production of BAFF leads to prevention and treatment of autoimmune diseases such as SLE, RA and SS, and thus there is demand for establishment of a system for accurately screening the suppression or inhibition of expression or production of BAFF.

For establishment of such screening system, it is possible to anticipate, for example, a method of obtaining a cell expressing BAFF stably by transforming a cultured cell with a gene vector constructed so as to express BAFF by recombinant DNA techniques. There is however a problem that even if BAFF could be expressed, BAFF would not always released extracellularly in a secretory form and would be uncertain as to whether the cultured cell can be a cell strain stable for expression and production of BAFF. Accordingly, none of such system has been reported. For example, if it would be possible to construct a system wherein the induction of intracellular expression of BAFF and the extracellular release of a detectable sufficient amount of BAFF can be recognized when a commercial cell strain is subjected to suitable stimulating conditions, the problem described above could be solved.

DISCLOSURE OF INVENTION

The object of the present invention is to provide a method of screening a substance suppressing or inhibiting the expression or production of BAFF by constructing a system wherein a detectable sufficient amount of BAFF is stably released extracellularly by subjecting a commercial cell strain to suitable stimulating conditions. By constructing such system, there can also be provided a method of screening a prophylactic/therapeutic agent for autoimmune diseases such as systemic lupus erythematosus (SLE), chronic rheumatoid arthritis (RA), Sjogren's syndrome (SS), autoimmune diabetes, AIDS, and an autoimmune disease accompanied by B-cell activation.

Accordingly, the present inventors made extensive study on selection of a cell strain and a method of stimulating the cell, and as a result, found that when a Loucy cell or Jurkat cell that is a commercial human T cell strain highly expressing CD3 is stimulated with an anti-CD3 antibody and/or a combination of TPA (12-O-tetradecanoylphorbol 13-acetate, or Phorbol 12-myristate 13-acetate, also expressed as PMA) with ionomycin, the induction of stable BAFF expression in the cell is recognized and simultaneously a detectable sufficient amount of BAFF can be stably released into a culture, and the present invention was thereby completed.

That is, the present invention provides a BAFF production system wherein a cultured human T cell is stimulated by adding a combination of TPA with ionomycin and/or an anti-CD3 antibody to the cell. Specifically, the present invention provides a BAFF production system wherein a cultured human T cell such as Loucy cell or Jurkat cell is stimulated by adding a combination of TPA with ionomycin and/or an anti-CD3 antibody to the cell.

The present invention also relates to a method of inducing the production of BAFF in a cultured human T cell, by adding a combination of TPA with ionomycin and/or an anti-CD3 antibody to the cell. Specifically, the present invention relates to a method of inducing the production of BAFF in a cultured human T cell such as Loucy cell or Jurkat cell, by adding a combination of TPA with ionomycin and/or an anti-CD3 antibody to the cell.

The present invention also provides a method of screening a substance capable of regulating the expression or activity of BAFF in a BAFF production system wherein a cultured human T cell is stimulated by adding a combination of TPA with ionomycin and/or an anti-CD3 antibody to the cell. Specifically, the present invention provides a method of screening a substance capable of suppressing or inhibiting the expression or activity of BAFF in a BAFF production system wherein a cultured human T cell is stimulated by adding a combination of TPA with ionomycin and/or an anti-CD3 antibody to the cell. More specifically, the present invention provides a method of screening a substance capable of regulating, preferably suppressing or inhibiting the expression or activity of BAFF in a BAFF production system wherein a cultured human T cell such as Loucy cell or Jurkat cell is stimulated by adding a combination of TPA with ionomycin and/or an anti-CD3 antibody to the cell.

The screening method of the present invention relates particularly to a method of screening a substance capable of regulating the expression or activity of BAFF, which includes adding a test substance to a BAFF production system in which a combination of TPA with ionomycin and/or an anti-CD3 antibody are/is added to a cultured human T cell and then measuring the expression level and/or activity level of BAFF in the BAFF production system. Specifically, the present invention relates to a method of screening a substance capable of regulating the expression or activity of BAFF, which includes adding a test substance to a BAFF production system in which a combination of TPA with ionomycin and/or an anti-CD3 antibody are/is added to a cultured human T cell such as Loucy cell or Jurkat cell and then measuring the expression level and/or activity level of BAFF in the BAFF production system. More specifically, the present invention relates to a method of screening a substance capable of suppressing or inhibiting the expression or activity of BAFF, which includes adding a test substance to a BAFF production system in which a combination of TPA with ionomycin and/or an anti-CD3 antibody are/is added to a cultured human T cell such as Loucy cell or Jurkat cell and then measuring the expression level and/or activity level of BAFF in the BAFF production system.

Further, the present invention provides a method of screening a prophylactic/therapeutic agent for autoimmune diseases such as systemic lupus erythematosus (SLE), chronic rheumatoid arthritis (RA), Sjogren's syndrome (SS), autoimmune diabetes, AIDS, and an autoimmune disease accompanied by B-cell activation, in a BAFF production system wherein a cultured human T cell is stimulated by adding a combination of TPA with ionomycin and/or an anti-CD3 antibody to the cell. Specifically, the present invention provides a method of screening a prophylactic/therapeutic agent for autoimmune diseases such as systemic lupus erythematosus (SLE), chronic rheumatoid arthritis (RA), Sjogren's syndrome (SS), autoimmune diabetes, AIDS, and an autoimmune disease accompanied by B-cell activation, in a BAFF production system wherein a cultured human T cell such as Loucy cell or Jurkat cell is stimulated by adding an anti-CD3 antibody and/or a combination of TPA with ionomycin to the cell. More specifically, the present invention provides a method of screening a prophylactic/therapeutic agent for autoimmune diseases such as systemic lupus erythematosus (SLE), chronic rheumatoid arthritis (RA), Sjogren's syndrome (SS), autoimmune diabetes, AIDS, and an autoimmune disease accompanied by B-cell activation, which includes adding a test substance to a BAFF production system in which a combination of TPA with ionomycin and/or an anti-CD3 antibody are/is added to a cultured human T cell such as Loucy cell or Jurkat cell and then measuring the expression level and/or activity of BAFF in the BAFF production system.

Further, the present invention relates to a BAFF production inducer for a BAFF-producing cell, which contains a combination of TPA with ionomycin and/or an anti-CD3 antibody. Specifically, the present invention relates to a BAFF production inducer for a cultured human T cell, which contains a combination of TPA with ionomycin and/or an anti-CD3 antibody. More specifically, the present invention relates to a BAFF production inducer for a cultured human T cell such as Loucy cell or Jurkat cell, which contains a combination of TPA with ionomycin and/or an anti-CD3 antibody.

According to the present invention, there can be provided a method of screening, with a cultured cell strain, a substance capable of suppressing or inhibiting the production of BAFF as well as a method of screening a prophylactic/therapeutic agent for diseases involved in production or activity of BAFF, such as systemic lupus erythematosus (SLE), chronic rheumatoid arthritis (RA), Sjogren's syndrome (SS), autoimmune diabetes, AIDS, and an autoimmune disease accompanied by B-cell activation.

BEST MODE FOR CARRYING OUT THE INVENTION

Figure 1:
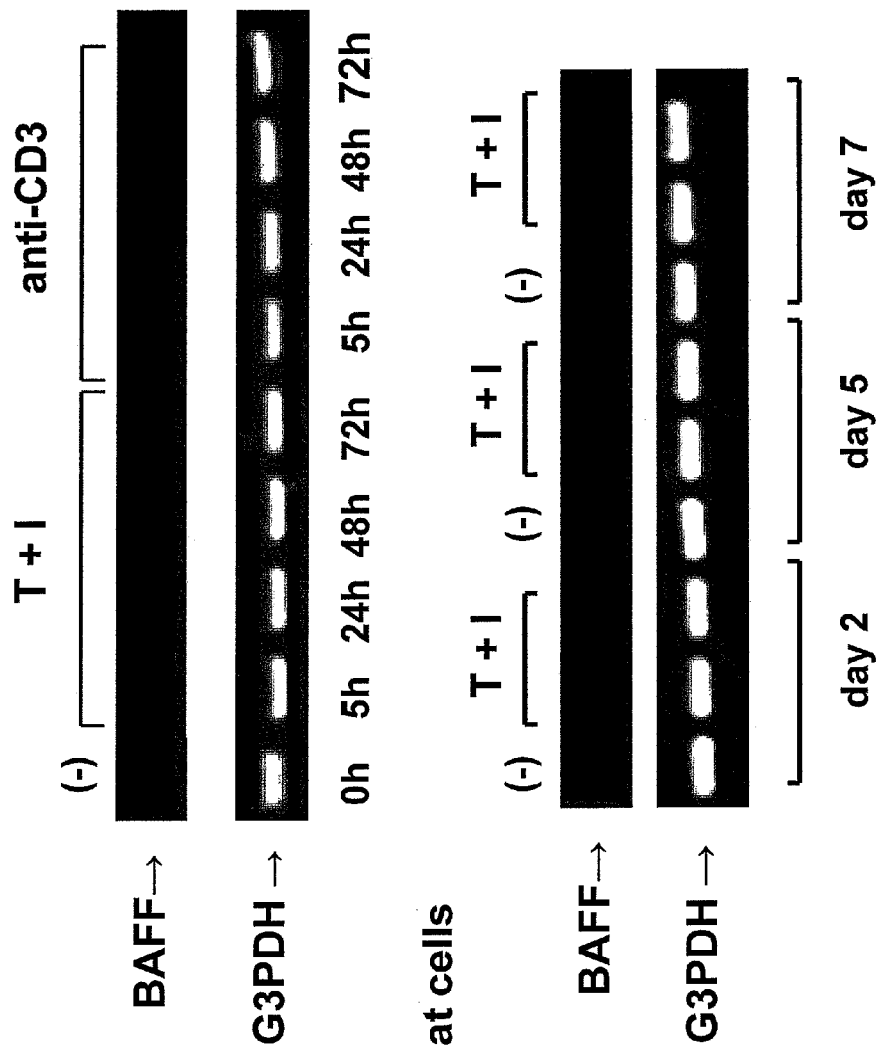
FIG. 1 is a drawing showing the expression of BAFF upon stimulation of a Loucy cell or Jurkat cell with an anti-CD3 antibody or both TPA and ionomycin.

The inventors examined the expression of BAFF upon stimulation of a Loucy cell or Jurkat cell with various substances. As a result, the inventors found that when a Loucy cell or Jurkat cell is stimulated with an anti-CD3 antibody or a combination of TPA with ionomycin, the induction of stable BAFF expression in the cell is recognized and simultaneously a detectable sufficient amount of BAFF can be stably released into a culture, as shown later in the Examples.

Accordingly, the method of screening a substance capable of regulating, preferably suppressing or inhibiting the expression or activity of BAFF can be constituted as follows.

That is, commercial human T cells are suspended at a suitable density in a suitable medium, then seeded in a culture plate or the like, and stimulated by adding TPA (final concentration of 0.001 to 1.0 µg/mL, preferably 0.005 to 0.1 µg/mL) and ionomycin (final concentration of 0.01 to 10.0 µg/mL, preferably 0.05 to 1.0 µg/mL), and a test substance (any concentration gradients at a final concentration of $10^{-15}$ to $10^{-3}$ M) is added as necessary, and culture of the cells is initiated. The culture supernatant is recovered 1 hour to 7 days, preferably 3 hours to 5 days, after the culture is initiated, and the concentration of BAFF in the supernatant can be measured and compared with the control, thereby measuring the activity of the test substance to suppress or inhibit BAFF in this screening system. For carrying out the above-described system, a culture plate coated previously with an anti-CD3 antibody diluted with PBS or the like (final concentration of 0.01 to 1000 µg/mL, preferably 0.1 to 100 µg/mL) may be used. The culture plate or the like coated with an anti-CD3 antibody can be used to detect a sufficient amount of BAFF without using TPA and ionomycin and is useful as an easier screening system.

The human T cell strain used in the present invention is preferably a commercial cell, and examples include a Loucy cell (ATCC Cat. No. CRL-2629), a Jurkat cell (ATCC Cat. No. TIB-152) and a TALL-1 cell (JCRB 0086), among which the Loucy cell (ATCC Cat. No. CRL-2629) or Jurkat cell (ATCC Cat. No. TIB-152) highly expressing CD3 and expected to be activated via a T-cell receptor is more preferable.

The anti-CD3 antibody used in the present invention includes an antihuman CD3 monoclonal antibody and antihuman CD3 polyclonal antibody produced by methods known by those skilled in the art, among which an antihuman CD3 monoclonal antibody is preferable, and a mouse antihuman CD3 monoclonal antibody (BD Pharmingen Cat No. 555336, or the like) is more preferable.

TPA used in the present invention, which is an abbreviation of 12-O-tetradecanoylphorbol 13-acetate, is a phorbol ester also known as phorbol 12-myristate 13-acetate (abbreviated sometimes as PMA), and TPA used in the present invention may be any of compounds given such names and also includes stereoisomers. Preferable commercial TPA includes, for example, 4-α-phorbol 12-myristate 13-acetate (SIGMA Cat. No. P-148).

Ionomycin used in the present invention is a polyether antibiotic derived from *Streptomyces conglobatus* and is known to act as calcium ionophore, and ionomycin used in the present invention also includes pharmaceutically acceptable salts. Preferable commercially available ionomycin includes, for example, ionomycin, calcium salt (SIGMA Cat. No. IO634).

There is a characteristic that BAFF production inducer of the present invention contains a combination of TPA with ionomycin and/or an anti-CD3 antibody as active ingredients for inducing the production of BAFF. The BAFF production inducer of the present invention can comprise, in addition to the above active ingredients, a carrier such as a buffer solution which can be added to a cell system, and together with the carrier which can be added to a cell system, can be formed into a composition for inducing the production of BAFF.

The BAFF production inducer of the present invention can be applied to a BAFF-producing cell, preferably a cultured cell, and preferable examples of the cell include a cultured human T cell, specifically a Loucy cell and Jurkat cell.

When the BAFF production inducer of the present invention includes a combination of TPA with ionomycin as the active ingredients, the respective active ingredients are used by adding them to a cell system in such amounts that the final concentration of TPA becomes 0.001 to 1.0 µg/mL, preferably 0.005 to 0.1 µg/mL, while the final concentration of ionomycin becomes 0.01 µg/mL to 10 µg/mL, preferably 0.05 µg/mL to 1 µg/mL. When the active ingredient is an anti-CD3 antibody, the active ingredient can be put to a culture plate at a concentration of 0.1 µg/mL to 100 µg/mL, preferably 1 µg/mL to 30 µg/mL in a buffer solution.

The thus obtained BAFF production system of the present invention has a surprising feature that a detectable sufficient amount of BAFF can be stably released into a culture as shown later in the Examples, and thus it is possible to realize not only a method of screening a substance capable of regulating, preferably suppressing or inhibiting the expression or activity of BAFF, but also a method of screening a prophylactic/therapeutic agent for autoimmune diseases such as systemic lupus erythematosus (SLE), chronic rheumatoid arthritis (RA), Sjogren's syndrome (SS), autoimmune diabetes, AIDS, and an autoimmune disease accompanied by B-cell activation.

EXAMPLES

Hereinafter, the present invention is described in more detail by reference to the Examples, but the technical scope of the present invention is not limited by the Examples.

Example 1

Expression of BAFF Upon Stimulation of a Loucy Cell or Jurkat Cell with an Anti-CD3 Antibody or Both TPA and Ionomycin (a) Culture Under Stimulation with TPA and Ionomycin Loucy cells or Jurkat cells purchased from ATCC (American Type Culture Collection) were suspended in RPMI1640 medium containing 10% FBS (Fetal bovine serum), 0.45% D-glucose, 1 mM sodium pyruvate and 1 mM HEPES and seeded at a density of $1 \times 10^6$ cells/well on a 6-well culture plate. The cells were recovered 5 hours, 24 hours, 48 hours and 72 hours (Loucy cells) or 48 hours, 120 hours and 168 hours (Jurkat cells) after the culture was initiated. Total RNA was extracted from these recovered cells, and BAFF mRNA was analyzed by the RT-PCR method under the following conditions. Using ReverTra Dash kit (TOYOBO Cat. No. PCR-401), the sample was subjected to reverse transcription reaction at 30° C. for 10 minutes, at 42° C. for 20 minutes and at 99° C. for 5 minutes to give cDNA. Using Advantage 2 PCR Enzyme system (BD Biosciences Cat. No. PT3281-1), this cDNA was reacted at 94° C. for 1 minute, then subjected to 35 reaction cycles each at 94° C. for 30 seconds and at 66° C. for 1.5 minutes and reacted at 66° C. for 5 minutes, and the DNA thus acquired was separated by 1.5% agarose gel electrophoresis, and an objective band was recognized at a position of 975 bp. The primer sequences used in the PCR reaction are as follows:

```
Forward: 5'-aggccccaaccttcaaagttcaag  (SEQ ID NO: 1)

Reverse: 5'-cttagaggtacagagaaagggagg  (SEQ ID NO: 2)
```

The results are shown in FIG. 1. FIG. 1(*a*) shows the sample from the Loucy cells, and FIG. 1(*b*) shows the sample from the Jurkat cells. In each profile, G3PDH is a positive control. In Loucy cells and Jurkat cells stimulated with TPA and ionomycin, the expression of BAFF mRNA was recognized 5 hours and 2 days after the stimulation, and the induction of evident expression of BAFF mRNA by TPA and ionomycin was continuously recognized over 72 hours and 7 days (168 hours) after the culture was initiated, as shown in FIG. 1(a) and (b). It was thus found that because the induction of stable expression of BAFF was recognized by culturing Loucy cells or Jurkat cells under stimulation with TPA and ionomycin, this culture system can be used in screening a substance suppressing or inhibiting the expression of BAFF.

(b) Culture Under Stimulation with an Anti-CD3 Antibody

An anti-CD3 antibody diluted at 10 μg/mL with PBS was put to a 6-well plate and adsorbed onto the bottom at 4° C. overnight, and then Loucy cells suspended in the same manner as in (a) were seeded at a density of $1 \times 10^6$ cells/well. The cells were recovered 5 hours, 24 hours, 48 hours and 72 hours after the culture was initiated. Total RNA was extracted from these recovered cells, and BAFF mRNA was analyzed by the RT-PCR method under the following conditions. Using ReverTra Dash kit (TOYOBO Cat. No. PCR-401), the sample was subjected to reverse transcription reaction at 30° C. for 10 minutes, at 42° C. for 20 minutes and at 99° C. for 5 minutes to give cDNA. Using Advantage 2 PCR Enzyme system (BD Biosciences Cat. No. PT3281-1), this cDNA was reacted at 94° C. for 1 minute, then subjected to 35 reaction cycles each at 94° C. for 30 seconds and at 66° C. for 1.5 minutes and reacted at 66° C. for 5 minutes, and the acquired DNA was separated by 1.5% agarose gel electrophoresis, and an objective band was recognized at a position of 975 bp. As a result, two-phase expression was made evident as shown in anti-CD3 in the right in FIG. 1(a), wherein the expression of BAFF mRNA is recognized from 5 hours after stimulation, thereafter the expression is attenuated, and the mRNA is expressed again 72 hours after the culture is initiated. There would be a possibility that such expression modes are different in biological meaning, and it is considered that the expression of BAFF induced by culturing Loucy cells under stimulation with an anti-CD3 antibody can be used in screening a substance suppressing or inhibiting the unique expression of BAFF.

Example 2

Figure 2:
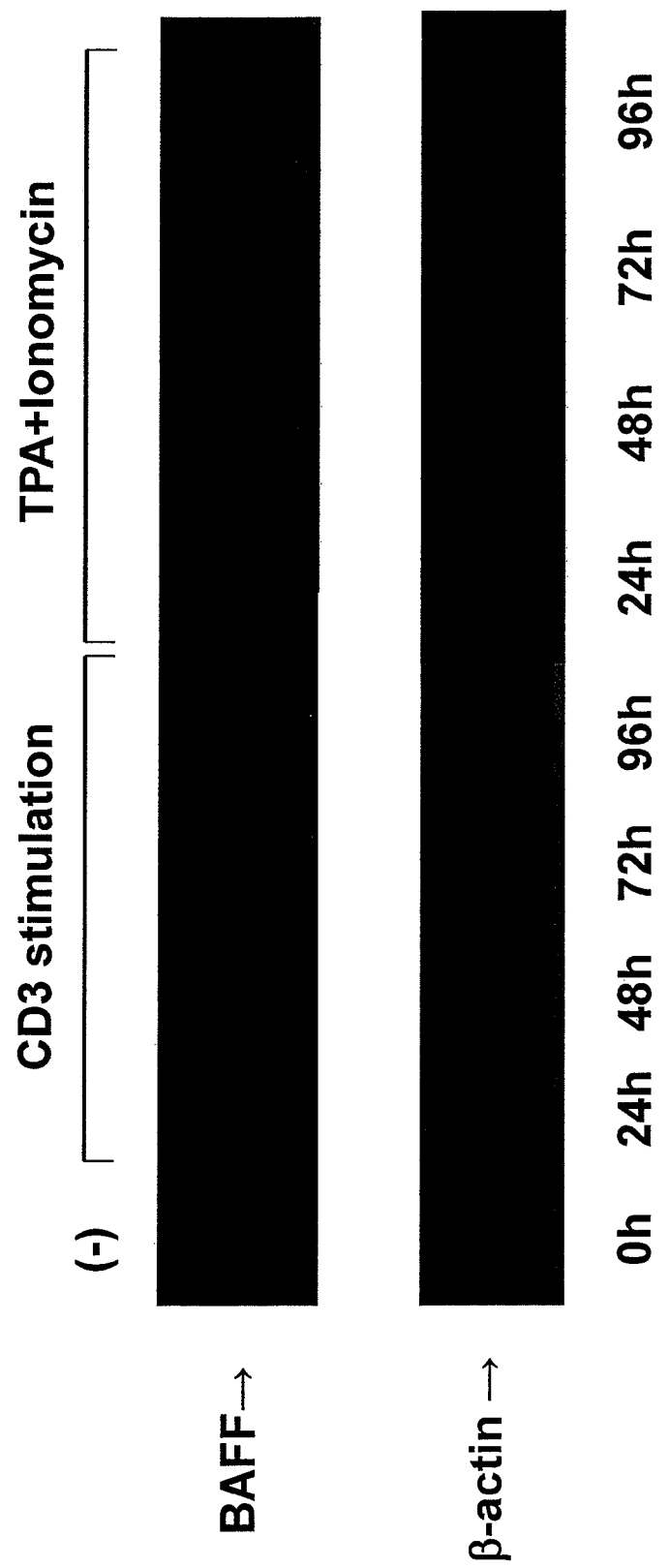
FIG. 2 is a drawing showing the expression of BAFF protein upon stimulation of a Loucy cell with an anti-CD3 antibody or both TPA and ionomycin.

Expression of BAFF Protein Upon Stimulation of a Loucy Cell with an Anti-CD3 Antibody or Both TPA and Ionomycin An anti-CD3 antibody diluted at 10 μg/mL with PBS was put to a 6-well plate and adsorbed onto the bottom at 4° C. overnight, and then Loucy cells suspended in the same manner as in Example 1 were seeded at a density of $1 \times 10^6$ cells/well. The cells were recovered 24 hours, 48 hours, 72 hours and 96 hours after the culture was initiated. These recovered cells were used and examined for expression of BAFF protein by a conventional Western blotting method. As an antibody for detection of BAFF protein, a rabbit antihuman BAFF polyclonal antibody (AB16530, manufactured by Chemicon) was used. The results are shown in FIG. 2. A control not stimulated is shown in (−) in the left in FIG. 2, and CD3 stimulation in FIG. 2 shows stimulation with anti-CD3 antibody, and TPA+Ionomycin shows stimulation with TPA and ionomycin. β-actin in the lower profile in FIG. 2 shows a positive control. In the Loucy cells stimulated with an anti-CD3 antibody, a 34-kDa band corresponding to human BAFF was confirmed from 24 hours after stimulation, and this evident expression induction was continuously recognized over 96 hours after the culture was initiated. Separately, Loucy cells were suspended in RPMI1640 medium containing 10% FBS (fetal bovine serum), 0.45% D-glucose, 1 mM sodium pyruvate and 1 mM HEPES and seeded at a density of $1 \times 10^6$ cells/well on a 6-well culture plate, and at the same time, simultaneously TPA and ionomycin were added to final concentrations of 0.05 μg/mL and 0.5 μg/mL respectively, and the cells were recovered 24 hours, 48 hours, 72 hours and 96 hours after the culture was initiated. These recovered cells were used and examined for expression of BAFF protein by a conventional Western blotting method. In the Loucy cells stimulated with TPA and ionomycin, a 34-kDa band corresponding to human BAFF was recognized from 24 hours after stimulation, and this evident expression induction was continuously recognized over 96 hours after the culture was initiated, as shown in FIG. 2. In these results, the induction of stable expression of BAFF protein by culturing Loucy cells under stimulation with an anti-CD3 antibody or both TPA and ionomycin was recognized over 96 hours after the culture was initiated, and this culture system can be used in screening a substance suppressing or inhibiting the expression of BAFF protein.

Reference Example 1

Preparation of Antihuman BAFF Monoclonal Antibody (4H4)

The antihuman BAFF monoclonal antibody (4H4) used in Example 3 was prepared in the following manner. That is, 13 amino acids (SEQ ID NO: 4) corresponding to a region, in the vicinity of a membrane, of an extracellular domain in 285 amino acids of BAFF shown in SEQ NO: 3 in the Sequence Listing were selected, then conjugated with KLH by the MBS method, and used as antigen. 100 μL of 1 mg/ml aqueous solution of the antigen peptide in physiological saline and Freund's complete adjuvant were formed into an emulsion and then used in intraperitoneally immunizing a mouse (Balb/c, 6-week-old). After 2 weeks, 100 μL of 1 mg/ml of an aqueous solution of the antigen peptide in physiological saline and Freund's complete adjuvant, which had been emulsified by sonication, were used as booster for additional immunization, followed by additional immunization twice at 2-week intervals. Two months after the first immunization, the spleen was excised, and lymphocytes were separated in RPMI 1640 medium (containing penicillin and streptomycin). The separated lymphocytes were fused with mouse bone marrow-derived myeloma cell P3U1 strain by the polyethylene glycol (PEG) method to prepare hybridoma cells. The hybridoma cells were suspended in a feeder cell-containing HAT medium, pipetted to a 96-well plate (Greiner) and cultured for 15 days. A culture supernatant was recovered from the wells in which the hybridoma cells had been cultured, and antibody-producing cells reactive with the antigen peptide were selected by ELISA (enzyme-linked immunosorbent assay). That is, first, 50 μL of 10 μg/mL antigen peptide was put to each well of the 96-well plate, adsorbed onto the bottom at 4° C. overnight and blocked with 100 μL of 2% BSA/PBS at 37° C. for 2 hours. Each well was reacted at 4° C. overnight with 100 μl supernatant of the hybridoma cells and then reacted at 37° C. for 1 hour with a 1000-fold dilution of HRP-labeled anti-mouse IgG and colored with orthophenylene diamine as substrate. After the reaction was terminated with 50 μL of 2 N sulfuric acid, each well was measured for absorption at 492 nm, and hybridomas showing an absorption of 1.0 or more were selected and cloned by limiting dilution.

The selected hybridoma cells were injected intraperitoneally to a mouse (Balb/c) to which 0.5 mL pristane had been intraperitoneally administered before 7 days and before 3 days, and about 10 days later, the ascites fluid was collected. The recovered ascites fluid was left at room temperature for 30 minutes, then left at 4° C. overnight, centrifuged at 15 Krpm for 10 minutes to recover a supernatant from which a mouse IgG fraction was separated and purified through a protein A-Sepharose column.

Figure 3:
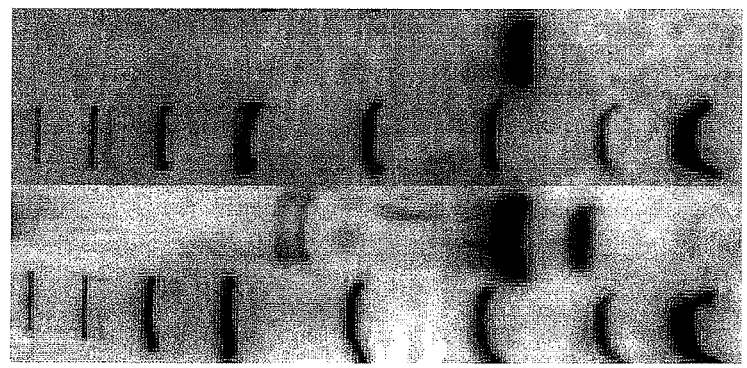
FIG. 3 is a drawing in which recombinant human BAFF (manufactured by Chemicon) was detected by conventional Western blotting method with an antihuman BAFF monoclonal antibody (4H4) and a control rabbit antihuman BAFF polyclonal antibody (Chem) manufactured by Chemicon.

By the method described above, a hybridoma cell strain producing the antihuman BAFF antibody (4H4 whose isotype is IgG1), as well as the antibody (4H4), was obtained. The resulting 4H4, and a control rabbit antihuman BAFF polyclonal antibody (AB16530: shown as Chem in FIG. 3) manufactured by Chemicon, were used in detection of recombinant human BAFF (manufactured by Chemicon) by the conventional Western blotting method. As a result, a 17-KDa band corresponding to the soluble human BAFF was confirmed as shown in FIG. 3.

Example 3

Production of BAFF Upon Stimulation of a Loucy Cell or Jurkat Cell with TPA and Ionomycin Loucy cells or Jurkat cells suspended in the same manner as in Example 1 were seeded to a 6-well culture plate at a density of $1 \times 10^6$ cells/well. At the same time, TPA and ionomycin were added to final concentrations of 0.05 μg/mL and 0.5 μg/mL respectively, and the culture supernatant was recovered 5 hours, 24 hours, 48 hours, 72 hours (Loucy cells) or 1, 4 and 7 days (Jurkat cells) after the culture was initiated. BAFF produced by the cells contained in these culture supernatants was measured by an ELISA method using a commercial rabbit antihuman BAFF polyclonal antibody (Cat No. AB16530, manufactured by Chemicon) and the mouse antihuman BAFF monoclonal antibody (4H4) prepared in Reference Example 1. The ELISA method was carried out in the following manner. That is, a 96-well plate was coated at 4° C. overnight with 1 μg/well rabbit antihuman BAFF polyclonal antibody (Cat. No. AB16530, manufactured by Chemicon) as primary antibody. Each well was washed 3 times with PBS containing 0.05% Tween 20, and then Block Ace (Dainippon Pharmaceutical Co., Ltd.) was added in a volume of 150 μL/well and reacted at 37° C. for 2 hours. Each well was washed 3 times with PBS containing 0.05% Tween 20, and 50 μL sample and 50 μl (8 ng/mL) of biotin-labeled 4H4 were added and reacted at room temperature for 2 hours. Each well was washed 3 times with PBS containing 0.05% Tween 20, and 50 μL of a 1000-fold dilution of streptoavidin-labeled HRP (Horse Radish peroxide) diluted with PBS containing 0.05% Tween 20 was added and reacted at room temperature for 30 minutes. Each well was washed 5 times with PBS containing 0.05% Tween 20, and then 50 μL of TMB One Solution (manufactured by Clonetech) was added and reacted for 5 minutes at room temperature, then 50 μL of 1 N HCl was added, and the each well was measured for absorbance at 450 nm with a plate reader (manufactured by Perkin Elmer). As a standard substance, recombinant human BAFF (Cat No. GF119, manufactured by Chemicon) was used to prepare a standard curve, from which the concentration of BAFF in the sample was measured.

Figure 4:
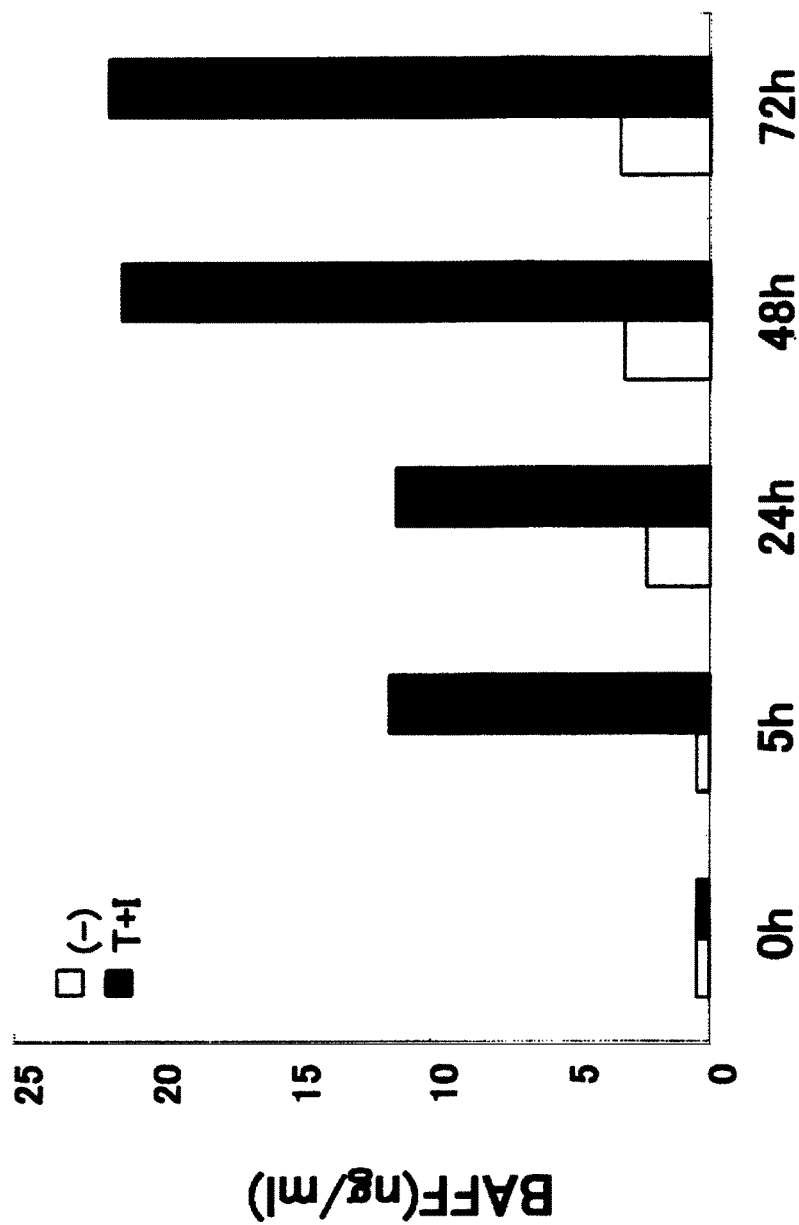
FIG. 4 is a graph showing the production of BAFF upon stimulation of a Loucy cell with TPA and ionomycin.
Figure 5:
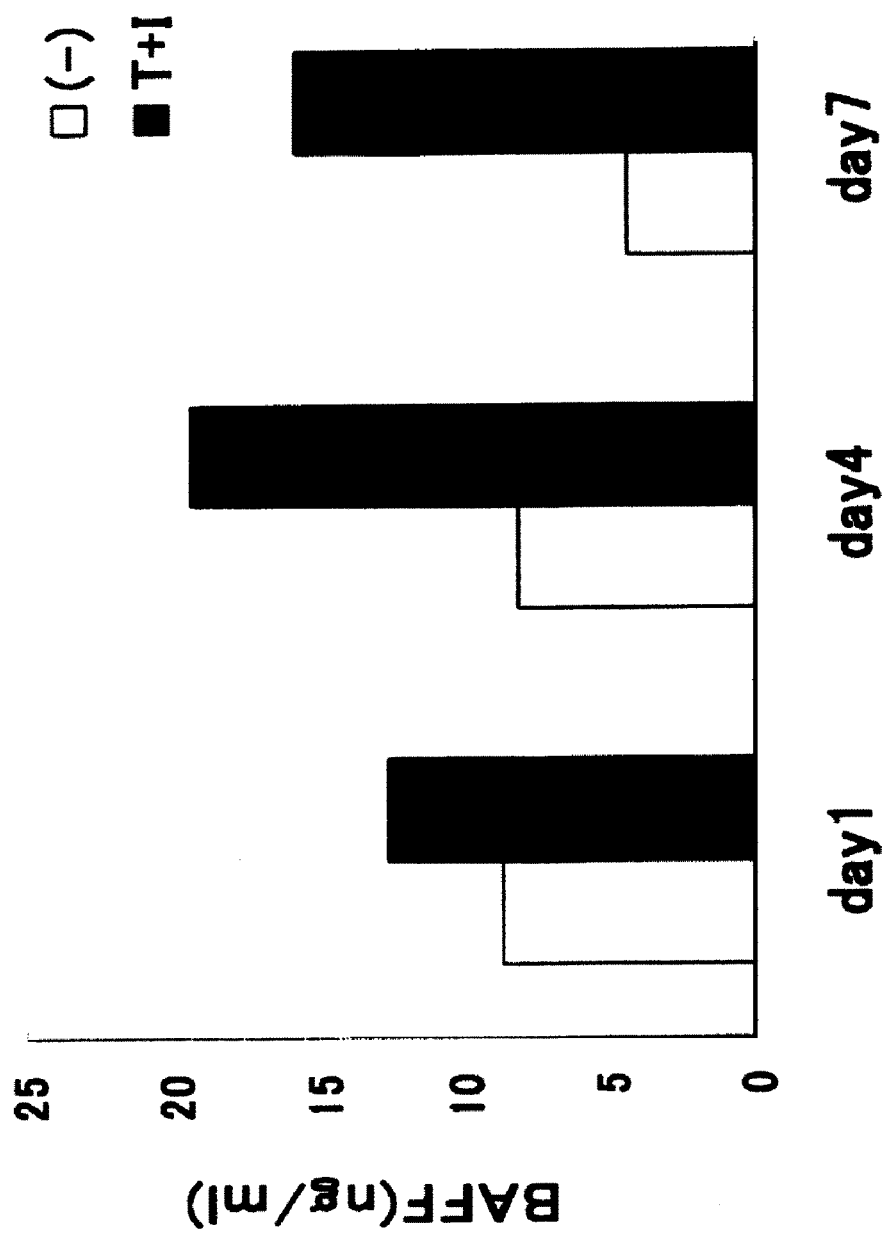
FIG. 5 is a graph showing the production of BAFF upon stimulation of a Jurkat cell with TPA and ionomycin.

A graph showing the result where the Loucy cells were used is shown in FIG. 4, and a graph showing the result where the Jurkat cells were used is shown in FIG. 5. The concentration of BAFF (ng/mL) is shown on the ordinate in each graph, and each left bar graph shows, as control, the concentration of BAFF without stimulation with TPA and ionomycin. The results indicated, as shown in FIGS. 4 and 5, that in the Loucy cells or Jurkat cells stimulated with TPA and ionomycin, BAFF in the culture supernatant can be detected from 5 hours or 1 day after stimulation and is continuously detected over 72 hours or 7 days after the culture was initiated. From these results, it was revealed that the induction of stable expression of BAFF was recognized by culturing Loucy cells or Jurkat cells under stimulation with TPA and ionomycin, and this culture system can be used in screening a substance suppressing or inhibiting the production of BAFF.

INDUSTRIAL APPLICABILITY

The present invention provides a method of inducing, in a cultured human T cell, the production of BAFF revealed to be related to autoimmune diseases such as systemic lupus erythematosus (SLE), chronic rheumatoid arthritis (RA), Sjogren's syndrome (SS), autoimmune diabetes, AIDS, and an autoimmune disease accompanied by B-cell activation, and provides a technique of screening a new substance useful for treatment and prevention of autoimmune diseases, and is industrially applicable.

The invention claimed is:

1. A method of inducing the production of B cell activating factor belonging to the tumor necrosis factor family (BAFF) in a Loucy cell, comprising:

adding 12-O-tetradecanoylphorbol 13-acetate (TPA) and ionomycin to the Loucy cell, thereby producing a detectable amount of BAFF in a culture of the Loucy cell or in the Loucy cell.

2. A method of screening a prophylactic/therapeutic agent for autoimmune diseases including systemic lupus erythematosus (SLE), chronic rheumatoid arthritis (RA), Sjogren's syndrome (SS), autoimmune diabetes, acquired immunodeficiency syndrome (AIDS) and an autoimmune disease accompanied by B-cell activation, the method comprising:

adding a test substance to a B cell activating factor belonging to the tumor necrosis factor family (BAFF) production system including a Loucy cell stimulated with 12-O-tetradecanoylphorbol 13-acetate (TPA) and ionomycin, and then measuring at least one of the expression level and activity of BAFF in a culture of the Loucy cell in the BAFF production system or in the Loucy cell in the BAFF production system, and determining that the test substance is a prophylactic/therapeutic agent for the autoimmune diseases if at least one of the expression level and activity of BAFF decreases in said culture of the cell.

3. The method according to claim 1, wherein the production of BAFF is detectable in the culture of the Loucy cell.

4. The method according to claim 2, wherein the measurement of the expression level and activity of BAFF is performed in the culture of the Loucy cell.

* * * * *

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<221> NAME/KEY: primer_bind
<223> OTHER INFORMATION: Forward primer of human BAFF

<400> SEQUENCE: 1
aggccccaac cttcaaagtt caag                                          24

<210> SEQ ID NO 2
<211> LENGTH: 24
<212> TYPE: DNA
<213> ORGANISM: Artificial Sequence
<220> FEATURE:
<221> NAME/KEY: primer_bind
<223> OTHER INFORMATION: Reverse primer of human BAFF
```

<400> SEQUENCE: 2
cttagaggta cagagaaagg gagg                                          24

<210> SEQ ID NO 3
<211> LENGTH: 285
<212> TYPE: PRT
<213> ORGANISM: Homo sapiens

<400> SEQUENCE: 3

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 4
<211> LENGTH: 13
<212> TYPE: PRT
<213> ORGANISM: Homo sapiens

<400> SEQUENCE: 4

Ala Val Gln Gly Pro Glu Glu Thr Val Thr Gln Asp Cys
1               5                   10